(12) United States Patent
Frechet et al.

(10) Patent No.: US 7,687,145 B2
(45) Date of Patent: Mar. 30, 2010

(54) COMPOUNDS CONTAINING A THIOL PROTECTED GROUP BONDED TO A PROTECTING GROUP VIA A POLARIZED BOND, AND STRUCTURE COMPRISING THE COMPOUNDS ON ITS SURFACE

(75) Inventors: Jean M. J. Frechet, Oakland, CA (US); Zachary M. Fresco, Santa Clara, CA (US)

(73) Assignee: The Regents of the University of California, Oakland, CA (US)

( * ) Notice: Subject to any disclaimer, the term of this patent is extended or adjusted under 35 U.S.C. 154(b) by 1011 days.

(21) Appl. No.: 11/244,446

(22) Filed: Oct. 4, 2005

(65) Prior Publication Data

US 2006/0273306 A1 Dec. 7, 2006

Related U.S. Application Data

(60) Provisional application No. 60/616,102, filed on Oct. 4, 2004.

(51) Int. Cl.
*B32B 5/16* (2006.01)
*C01F 7/02* (2006.01)
*C01F 7/08* (2006.01)

(52) U.S. Cl. ........................ 428/403; 428/221; 428/704; 556/427; 556/429; 556/437; 556/449; 556/465; 556/482; 556/489

(58) Field of Classification Search ................. 566/427, 566/429, 437, 449, 465, 482, 489; 428/221, 428/403, 704
See application file for complete search history.

(56) References Cited

U.S. PATENT DOCUMENTS

| 4,981,937 | A | * | 1/1991 | Kuriyama et al. | 526/328 |
| 5,670,581 | A | * | 9/1997 | Frechet et al. | 525/333.3 |
| 6,022,904 | A | * | 2/2000 | Sollradl et al. | 521/154 |
| 6,147,242 | A | * | 11/2000 | Batz-Sohn | 556/429 |
| 6,544,499 | B1 | * | 4/2003 | Glenn et al. | 424/70.1 |
| 7,030,271 | B2 | * | 4/2006 | Wessels et al. | 564/155 |
| 7,320,784 | B1 | * | 1/2008 | Pollak et al. | 424/9.1 |
| 7,332,619 | B2 | * | 2/2008 | Korth et al. | 556/426 |
| 2006/0052621 | A1 | * | 3/2006 | Korth et al. | 556/427 |
| 2006/0163564 | A1 | * | 7/2006 | Nothofer et al. | 257/40 |

OTHER PUBLICATIONS

Hicks, et al., "The Dynamics of Electron Self-Exchange between Nanoparticles", J. Am. Chem. Soc. 2001, 123, 7048-7053.
Wuelfing, et al., "Electron Hopping through Films of Arenethiolate Monolayer-Protected Gold Clusters," J. Phys. Chem. B 2002, 106, 3139-3145.
Maier, et al., "Local detection of electromagnetic energy transport below the diffraction limit in metal nanoparticle plasmon waveguides," Nature Materials 2003, 2, 229-232.

(Continued)

*Primary Examiner*—H. (Holly) T Le
(74) *Attorney, Agent, or Firm*—Withrow & Terranova, P.L.L.C.

(57) ABSTRACT

Organosulfur compounds suitable as protected thiol-containing reactive organic layer precursors, for example 3,5-dimethoxy-α,α-dimethylbenzyloxycarbonyl-3-mercapto-propyltriethoxysilane, are useful in methods of nanometer scale (nanoscale) patterning and fabrication of nanoscale structures on patterned surfaces. The compounds and methods enable the patternwise placement of nanoparticles, with nanometer resolution to form, for example, electrically conductive nanostructures.

12 Claims, 7 Drawing Sheets

OTHER PUBLICATIONS

Brongersma, et al., "Electromagnetic energy transfer and switching in nanoparticle chain arrays below the diffraction limit," Phys. Rev. B 2000, 62, R16356-R16359.

Mendes, et al., "Gold Nanoparticle Patterning of Silicon Wafers Using Chemical e-Beam Lithography", Langmuir 2004, 20, 3766-3768.

Demers, et al., "Orthogonal Assembly of Nanoparticle Building Blocks on Dip-Pen Nanolithographically Generated Templates of DNA," Angew. Chem. Int. Ed. 2001, 40, 3071-3073.

Mesquida, et al., "Maskless nanofabrication using the electrostatic attachment of gold particles to electrically patterned surfaces," Microelectronic Eng. 2002, 61-62, 671-674.

Liu, et al., "Planned Nanostructures of Colloidal Gold via Self-Assembly on Hierarchically Assembled Organic Bilayer Template Patterns with In-situ Generated Terminal Amino Functionality," Nanoletters 2004, 4, 845-851.

Fresco, et al., "AFM-Induced Amine Deprotection: Triggering Localized Bond Cleavage by Application of Tip/Substrate Voltage Bias for the Surface Self-Assembly of Nanosized Dendritic Objects," J. Am. Chem. Soc. 2004, 126.

Fresco et al., "Selective Surface Activation of a Functional Monolayer for the Fabrication of Nanometer Scale Thiol Patterns and Directed Self-Assembly of Gold Nanoparticles", JACS Communications, J.AM. Chem. Soc. 2005, 127-8302-8303.

Birr, C.et al., "Der αα-Dimethyl-3.5-dimethoxybenzyloxycarbonyl (Ddz)-Rest, eine photo- und säurelabile Stickoff-Schutzgruppe für die Peptidchemie*)*, Liebigs Ann. Chem. 1972, 763, 162-172.

Krämer, S. et al., "Scanning Probe Lithography Using Self-Assembled Monolayers" *Chem. Rev.* 2003, 103, 4367-4418.

Ma, Y. R. et al., "Tip-induced local anodic oxidation on the native $SiO_2$ layer of Si(111) using atomic force microscope", *Phys. Rev. B.* 2001, 64, 195324-1-195324-5.

Tully, D. C et al, "Synthesis and Preparation of Ionically Bound Dendrimer Monolayers and Application toward Scanning Probe Lithography", *Chem. Mater.* 1999, 11, 2892-2898.

Cameron, J.F. et al., "Base Catalysis in Imaging Materials. 1. Design and Synthesis of Novel Light-Sensitive Urethanes as Photoprecursors of Amines", *J. Org. Chem.*, 1990, 55, 5919-22.

Thompson, L. F. et al., *Introduction to Microlithography* $2^{nd}$ ed. Oxford University Press 1994.

\* cited by examiner

COMPOUNDS CONTAINING A THIOL PROTECTED GROUP BONDED TO A PROTECTING GROUP VIA A POLARIZED BOND, AND STRUCTURE COMPRISING THE COMPOUNDS ON ITS SURFACE

CROSS-REFERENCE TO RELATED APPLICATIONS

This application claims priority to U.S. Provisional Patent Application No. 60/616,102, filed Oct. 4, 2004, titled COMPOUND AND METHOD FOR NANOSCALE FORMATION WITH NANOPARTICLES, the disclosure of which is incorporated herein by reference in its entirety and for all purposes.

BACKGROUND OF THE INVENTION

The present invention relates generally to protected organosulfur compounds suitable as reactive layer precursors and methods of using the compounds in nanometer scale (nanoscale) patterning and fabrication of nanoscale structures on patterned surfaces.

Patterns of closely spaced gold or other nanoparticles have potential applications in nanoelectronics and photonics for example as electrically conducting wires or as plasmon wave guides for photonic devices. Previously, arbitrary patterns of gold nanoparticles (AuNPs) have been deposited onto a surface via e-beam lithography or dip-pen nanolithography. Many methods for performing tip-induced surface chemistry have also been described in the literature (see e.g., Krämer, S.; Fuierer, R. R.; Gorman, C. B. *Chem. Rev.* 2003, 103, 4367-4418; and references contained therein.) Some rely on the application of a voltage bias between a surface and the tip of an AFM to locally oxidize the surface, producing nanometer relief features. (see e.g., Ma, Y. R.; Yu, C.; Yao, Y. D.; Liou, Y.; Lee, S. F. *Phys. Rev. B.* 2001, 64, 195324-1-195324-5; and Tully, D. C.; Trimble, A. R.; Fréchet, J. M. J.; Wilder, K.; Quate, C. F. *Chem. Mater.* 1999, 11, 2892-2898.). Arbitrary patterns of AuNPs have been made on the sub 100 nm scale using E-beam lithography and dip-pen nanolithography, while patterns as small as 30 nm have been obtained using other scanning probe techniques. Also, regularly spaced AuNP arrays have been made by self-assembly onto templates.

Alternative materials and techniques for advancing this technology would be desirable.

SUMMARY OF THE INVENTION

The present invention relates generally to organosulfur compounds suitable as protected thiol-containing reactive organic layer precursors and methods of using these compounds in nanometer scale (nanoscale) patterning and fabrication of nanoscale structures on patterned surfaces. The compounds and methods enable the patternwise placement of nanoparticles, for example electrically conductive (e.g., metallic) nanoparticles, such as gold or silver nanoparticles (AuNPs or AgNPs) with nanometer resolution to form, for example, electrically conductive nanostructures.

A reactive organic layer containing a protected thiol is formed on a solid surface by application of a suitable organosulfur precursor compound to a surface that is prepared to react with and/or bind the precursor as a layer. The layer may be a monolayer or the top layer in a multilayer substrate. In a preferred embodiment, a reactive monolayer is formed on a planar solid surface by application of a monolayer precursor compound to the surface.

Thereafter, a pattern is defined using a scanning force microscopy (SFM) tool, such as an atomic force microscope (AFM), to apply a voltage bias between one or more tips and selected locations of a surface covered by the reactive organic layer containing the protected thiol, such as 3,5-dimethoxy-α,α-dimethylbenzyloxycarbonyl-3-mercaptopropyltriethoxysilane. During the voltage application, thiocarbonate moieties from the bound reactive layer are selectively transformed into thiols.

The patterned surface can then be used to direct the subsequent self-assembly of nanoparticles. This technique can be used to fabricate electrically conductive nanostructures composed of lines a single nanoparticle (e.g., 10 nm AuNP) in width as well as to control the placement of individual nanoparticles. Gold nanoparticles (e.g., 10 nm AuNPs) are a preferred nanoparticle in this application. However, the technique can also be used to fabricate patterns composed of nanoparticles of other metals (e.g., silver, copper, cobalt, etc.) or nanoparticle compositions (including semiconducting nanoparticles such as CdSe) that have an affinity for thiols or the disulfide compounds that are well known in the art to form from thiols by oxidation.

In one aspect, the invention relates to an organosulfur compound, comprising: a group configured to bind to a surface; a protected thiol functional group bonded to the surface binding group; and a protecting group bonded to the protected thiol functional group via a polarized bond labile to field stimulated cleavage.

In another aspect, the invention relates to a protected thiol-containing reactive organic layer composition, comprising: a substrate surface; and a layer of an organosulfur compound bound to the substrate surface.

In another aspect, the invention relates to a method of forming nanoscale patterns on a substrate surface, comprising: forming a protected thiol-containing reactive organic layer on the substrate surface; and patterning the protected thiol-containing reactive organic layer in an inert atmosphere with a scanning probe with a voltage potential between the probe and the surface to generate free surface-bound thiols. The method may further involve applying nanoparticles to the patterned monolayer to form self-assembled nanostructures.

In another aspect, the invention relates to a nanoscale structure, comprising self-assembled conductive nanoparticles on a substrate surface bound to the surface via activated portions of a protected organosulfur monolayer.

In additional aspects, the invention relates to: a monolayer precursor for use in nanoscale pattern formation with nanoparticles comprising DDZ (3,5-dimethoxy-α,α-dimethylbenzyloxycarbonyl) protected 3-mercaptopropyltriethoxysilane, and a method of forming the monolayer precursor comprising the steps of mixing 3,5-dimethoxy-α,α-dimethylbenzyl alcohol and 3-mercaptopropyltriethoxysilane with p-nitrophenyl chloroformate, as shown:

-continued

Also, the invention relates to a method of forming nanoscale patterns and structures of nanoparticles comprising the steps of: immersing a freshly hydroxylated silicon surface in a solution of DDZ (3,5-dimethoxy-α,α-dimethylbenzyloxycarbonyl) protected 3-mercaptopropyltriethoxysilane; patterning the surface with a scanning probe with a voltage potential between the probe and the surface (e.g., 12 V applied to the surface with a grounded probe) to activate regions of the compound precursor; and immersing the patterned surface in an aqueous solution of citrate ligated gold nanoparticles. The method may further involve plating a metal on the patterned surface after immersion.

These and other features of the invention are further described and exemplified in the detailed description below.

DETAILED DESCRIPTION OF SPECIFIC EMBODIMENTS

Reference will now be made in detail to specific embodiments of the invention. Aspects of the specific embodiments are illustrated in the accompanying drawings. While the invention will be described in conjunction with these specific embodiments, it will be understood that it is not intended to limit the invention to such specific embodiments. In the following description, numerous specific details are set forth in order to provide a thorough understanding of the present invention. The present invention may be practiced without some or all of these specific details. In other instances, well known process operations have not been described in detail in order not to unnecessarily obscure the present invention.

Introduction

Organosulfur compounds suitable as protected thiol-containing reactive organic layer precursors and methods of using these compounds in nanometer scale (nanoscale) patterning and fabrication of nanoscale structures on patterned surfaces are provided. The compounds and methods enable the patternwise placement of nanoparticles, for example electrically conductive (e.g., metallic) nanoparticles, such as gold or silver nanoparticles (AuNPs or AgNPs) with nanometer resolution to form, for example, electrically conductive nanostructures.

A reactive organic layer containing a protected thiol is formed on a solid surface by application of a suitable organosulfur precursor compound to a surface that is prepared to react with and bind the precursor as a layer. The layer may be a monolayer or the top layer in a multilayer substrate. In a preferred embodiment, a reactive monolayer is formed on a planar solid surface by application of a monolayer precursor compound to the surface.

Thereafter, a pattern is defined using a scanning force microscopy (SFM) tool, such as an atomic force microscope (AFM), to apply a voltage bias between one or more tips and selected locations of a surface covered by the reactive organic layer containing the protected thiol, such as 3,5-dimethoxy-α,α-dimethylbenzyloxycarbonyl-3-mercaptopropyltriethoxysilane. During the voltage application, thiocarbonate moieties from the bound reactive layer are selectively transformed into thiols.

The patterned surface can then be used to direct the subsequent self-assembly of nanoparticles. This technique can be used to fabricate electrically conductive nanostructures composed of lines a single nanoparticle (e.g., 10 nm AuNP) in width as well as to control the placement of individual nanoparticles. Gold nanoparticles (e.g., 10 nm AuNPs) are a preferred nanoparticle in this application. However, the technique can also be used to fabricate patterns composed of nanoparticles of other metals (e.g., silver, copper, cobalt, etc.) or nanoparticle compositions (including semiconducting nanoparticles such as CdSe) that have an affinity for thiols or disulfide compounds.

Reactive Layer Precursor and Synthesis

Figure 1:
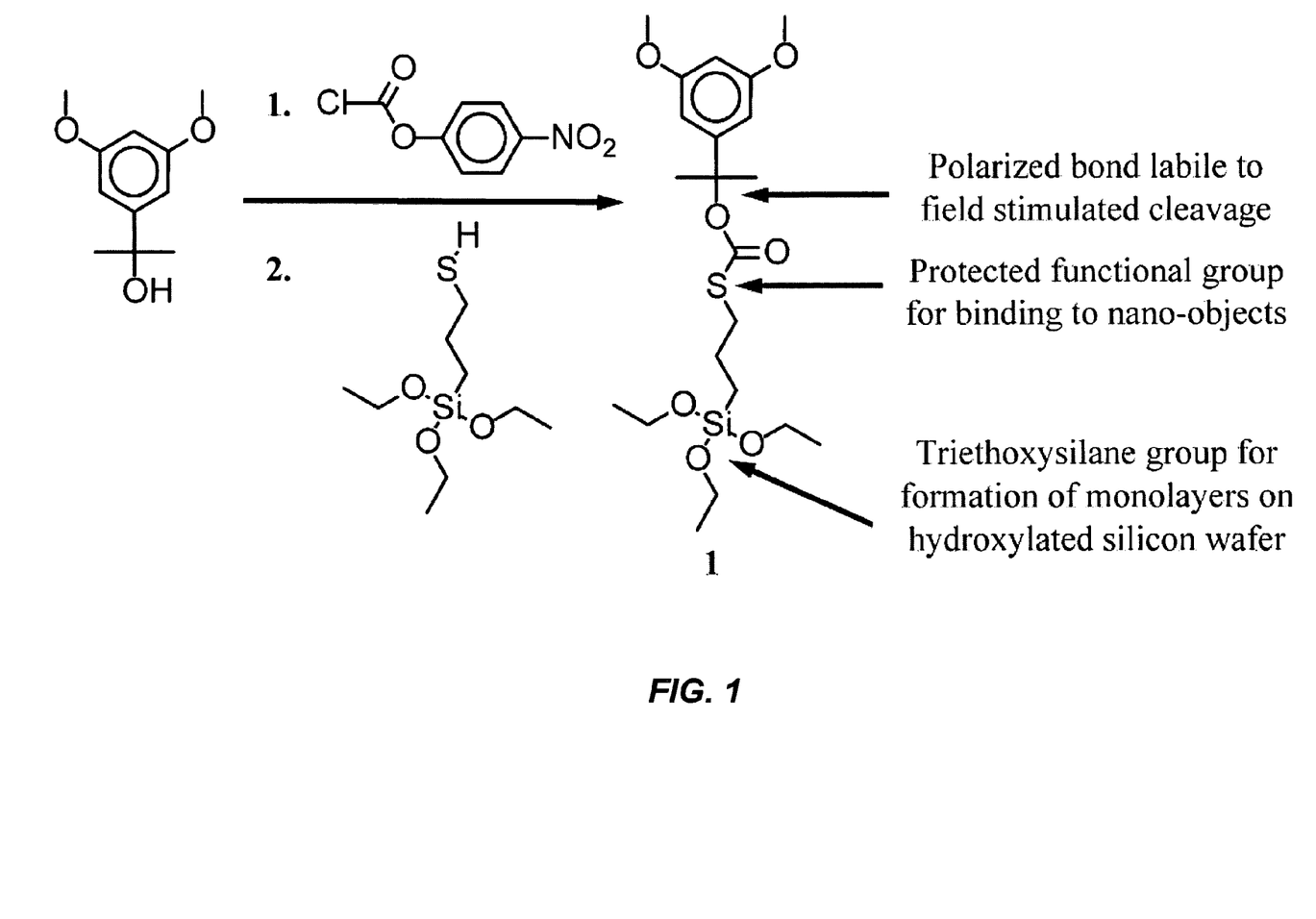
FIG. 1 illustrates a suitable precursor compound for a protected thiol monolayer in accordance with one aspect of the present invention, it synthesis and key characteristics.

The present invention relies on a voltage bias applied between a surface and a conducting scanning probe tip to selectively activate regions of a protected sulfur-containing reactive organic layer on the surface and release the free thiol. Referring to FIG. 1, a suitable precursor compound for such a layer, its synthesis and key characteristics are shown. A suitable precursor will have a group for binding to a surface to form layers, a protected thiol functional group bonded to the surface binding group, and a protecting group bonded to the protected thiol functional group via a polarized bond labile to field stimulated cleavage.

The illustrated example of FIG. 1 is 3,5-dimethoxy-α,α-dimethylbenzyloxycarbonyl-3-mercaptopropyltriethoxysilane, also referred to as DDZ-protected 3-mercaptopropyltriethoxysilane. This precursor is particularly well suited to binding to hydrolysable surface, such as silicon dioxide.

This precursor compound may be prepared in two steps from 3,5-dimethoxy-α,α-dimethylbenzyl alcohol and 3-mercaptopropyltriethoxysilane using p-nitrophenyl chloroformate. The triethoxysilane group binds to hydroxylated surfaces, such as a hydroxylated silicon wafer. Further synthetic details are provided in the Examples below.

Alternative protected sulfur-containing reactive organic layer precursor compounds may have organosilane groups other than triethoxysilane, such as alkyl chlorosilanes or alkyl alkoxysilanes (e.g., in which the ethyl groups are replaced by another alkyl group or a phenyl groups), amino silanes (e.g., dimethylaminosilane) and sila-imidazoles.

Thiols, and to a lesser extent disulfides obtained by spontaneous oxidation of thiols, are advantageously used in many implementations of this invention as they have a high affinity for many metals and metal oxides. Their affinity for gold and copper is particularly well recognized. As a result, electrically conductive metallic nanostructures are readily formed using the thiol precursors.

Reactive Layer Formation

Protected thiol-containing reactive organic layers may be formed by applying a solution of the layer precursor to a suitably prepared substrate surface. The reactive layer may be a monolayer applied directly to the surface of a substrate material, e.g., a planar surface such as a silicon wafer. Or it may be a top layer, applied to one or more other layers between the top layer and the substrate surface.

Application may be by way of immersion, spraying, painting, Langmuir-Blodgett assembly, or other coating technique know to those of skill in the surface chemistry arts. The substrate surface may be any material compatible with the processing techniques used to form the ultimate structure and its intended use. The substrate surface should be prepared to display a functional group that will react with the reactive layer precursor to form a bound reactive layer or the substrate surface should otherwise bind to the reactive layer precursor.

Figure 2:
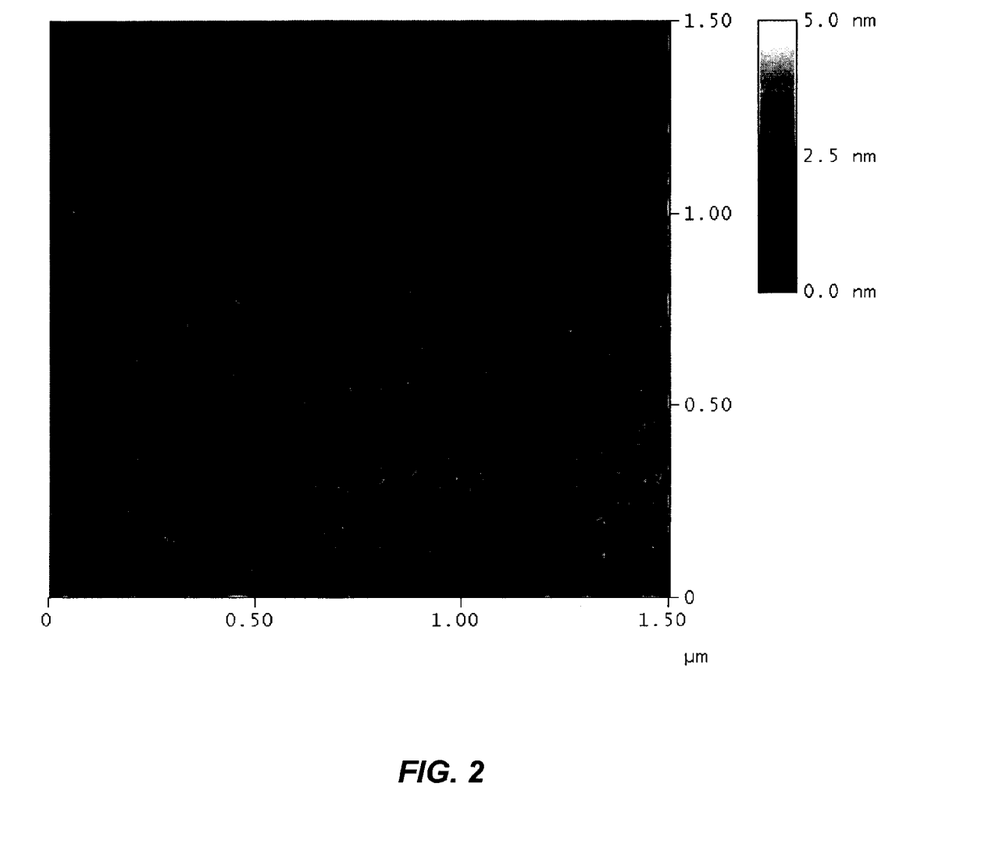
FIG. 2 illustrates an AFM height image of a DDZ-protected 3-mercaptopropyltriethoxysilane monolayer before patterning, in accordance with one aspect of the present invention.

In the case of the DDZ-protected 3-mercaptopropyltriethoxysilane precursor compound described above, the triethoxysilane group binds covalently to hydroxylated surfaces, and a suitable reactive layer, in this case a monolayer, may be prepared by immersing a freshly hydroxylated silicon surface in a solution of this precursor (e.g., 0.5% in dry toluene). FIG. 2 illustrates an AFM height image of the DDZ-protected 3-mercaptopropyltriethoxysilane monolayer on a silicon surface before patterning.

While a monolayer is illustrated in FIG. 2, as noted above, the reactive layer may also be a top layer, applied to one or more other layers between the top layer and the substrate surface. In addition, substrate surfaces other than silicon may be used. For an organosilane, any surface that can be modified by an organosilane may be used, including titania, tin oxide and many other metal oxides, and ITO (indium tin oxide). As will be understood by those skilled in the art of surface chemistry, alternative precursor compounds could have surface binding groups other than organosilanes suited to bonding to or coating other surface materials. These compounds and the associated methods otherwise in accordance with the process descriptions herein are considered to be within the scope of the present invention.

Reactive Layer Patterning and Structure Formation

Figure 3:
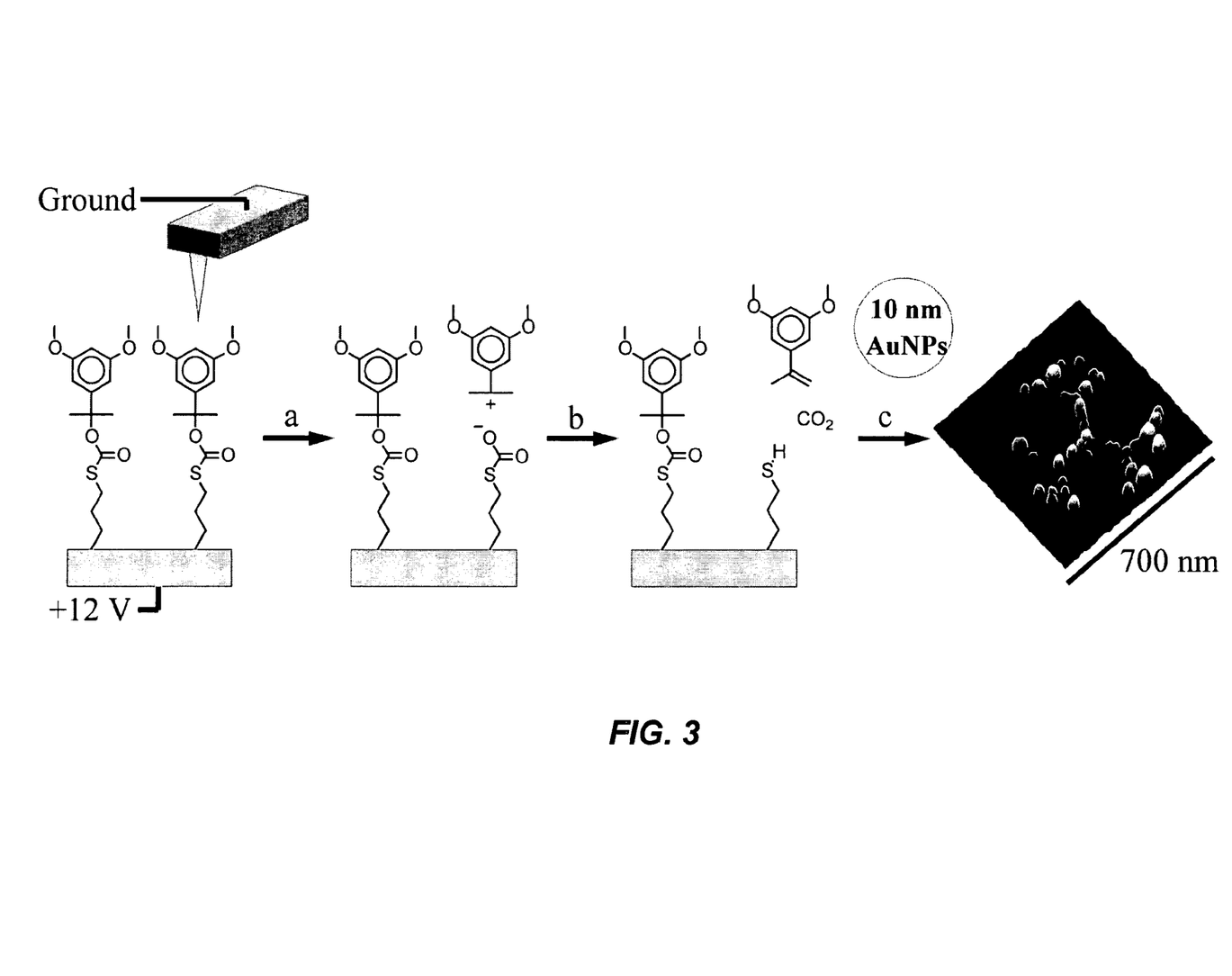
FIG. 3 illustrates the patterning of a surface bound protected thiol monolayer and fabrication of self-assembled nanostructures, in accordance with one aspect of the present invention.

The surface bound protected thiol-containing reactive organic layer may then be patterned with a scanning probe tool, as illustrated in FIG. 3. Surface patterning is conducted by application of a voltage potential between the probe tip and the surface to activate regions of the compound precursor. Effective patterning of the reactive layer may be conducted with the AFM amplitude set point reduced to about 10% of the imaging set point and traversing the grounded tip across the surface while a positive 12 V potential is applied to the substrate. The voltage required depends upon the distance between tip and surface and tip geometry. The sharper the tip and the closer it is held to the substrate surface, the lower the required voltage. A suitable voltage range is generally between about 0.5 and 20V, with a moderate value (e.g., 12V) being preferred in most typical applications using conventional equipment. The application of a voltage bias between the tip of an AFM and a silicon substrate in this way under an inert atmosphere (e.g., dry nitrogen) causes local activation of the thiol layer. Exposure to air may lead to spontaneous oxidation of thiols to a disulfide.

While the invention is not limited by any particular theory of operation, the DDZ protecting group has previously been employed as a photocleavable group in organic synthesis and lithography, though not to reveal a thiol or a disulfide as in the present invention. The accepted photochemical deprotection mechanism is heterolytic bond cleavage followed by release of carbon dioxide and elimination of a proton from the tertiary intermediate carbocation to produce 3,5-dimethoxy-α-methylstyrene. It is hypothesized that the intense local electric field between the tip and the surface may induce decomposition via a pathway analogous to photochemical deprotection, causing heterolytic bond cleavage and converting thiocarbonate moieties from the bound reactive layer into thiols.

It has been found that when ambient conditions are employed, oxidation of a susceptible underlying substrate, for example silicon, can obscure observation of the more subtle effects that the applied voltage bias may have on the reactive layer. However, in the absence of oxygen and water vapor, anodic oxidation of the underlying silicon (or other susceptible substrate material) can be prevented and it becomes possible to perform controlled chemistry on a surface bound protected thiol-containing reactive organic layer.

Following activation of the surface bound thiol-containing reactive organic layer by the tip, ligand exchange can be conducted to effect the deposition of nanoparticles only onto the free thiol regions, as further shown in FIG. 3. The patterned surface is used to direct the subsequent self-assembly of applied nanoparticles. In at least some cases, it may be necessary to treat the activated thiol layer surface with an aqueous solution of a mild reducing agent (e.g., immersion in DL-dithiothreitol (DTT) (10 mg/mL) for 24 hours) in order to transform any disulfides that may have formed back into thiols, since the newly exposed thiols may be converted rapidly into disulfides either through exposure to atmospheric oxygen or during the patterning step itself.

Application of nanoparticles may be by way of immersion, spraying, ink-jetting, painting or other techniques know to those of skill in the surface chemistry arts. Aqueous or organic conditions may be used. For example, an activated substrate may be immersed in an aqueous solution of citrate ligated gold nanoparticles (10 nm citrate-stabilized AuNPs) for 24 hours and then rinsed gently. AFM images of nanostructures produced according to this process are illustrated in FIGS. 4 and 5.

Figure 4:
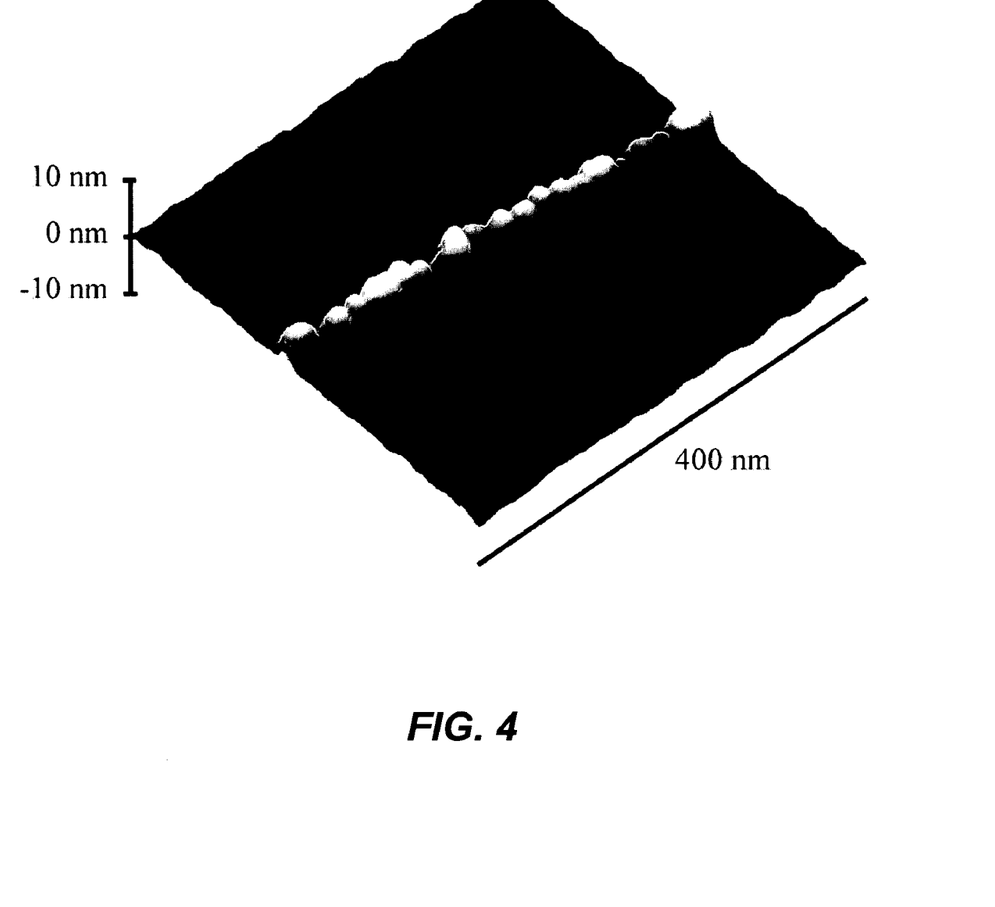
FIG. 4 shows an image of a line of close packed gold nanoparticles formed in accordance with one aspect of the present invention.
Figure 5:
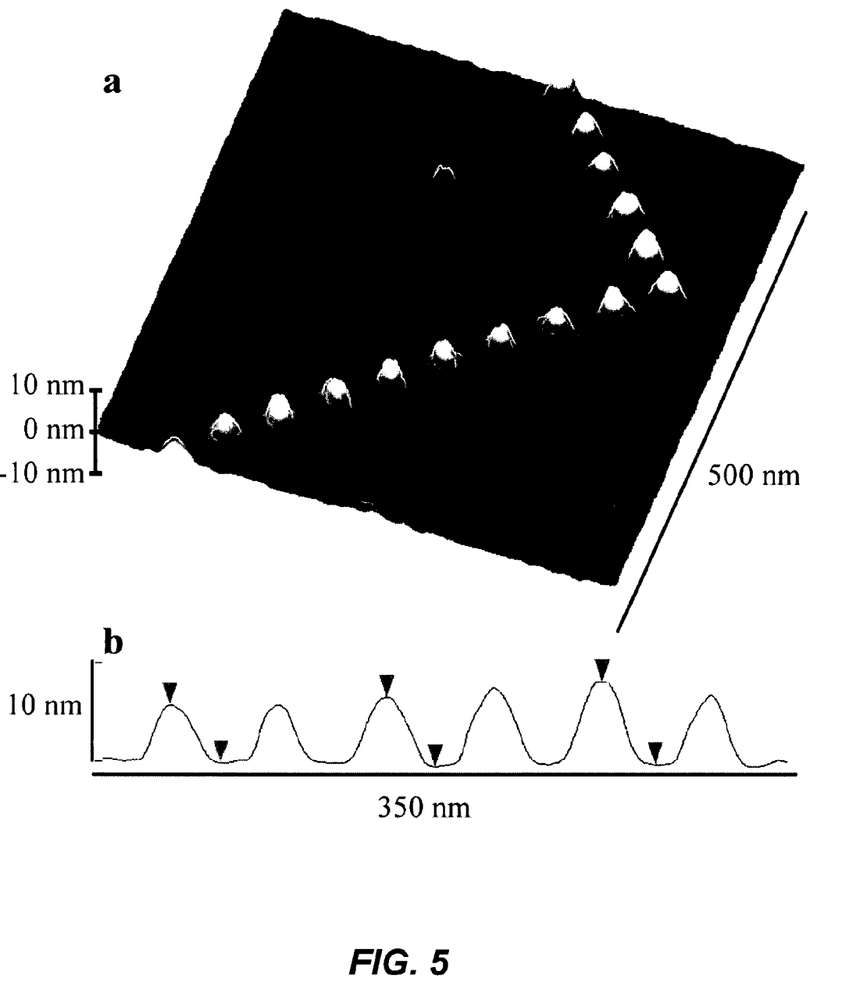
FIG. 5 shows individual gold nanoparticles intentionally placed at 50 nm intervals in accordance with one aspect of the present invention.

FIG. 4 shows an image of a line of close packed gold nanoparticles. It should be noted that this line has a width that corresponds to a single nanoparticle, demonstrating that this method is capable of producing lines of 10 nm or less depending also on the geometry of the tip. AuNP deposition follows the design defined by the field arising from the tip and therefore a great variety of patterns can be obtained.

It is also possible to control the placement of individual AuNPs on the surface by the programmed application of electrical pulses to the surface. For example individual gold nanoparticles intentionally placed at 50 nm intervals are shown in FIG. 5. The observed size variation in gold nanoparticles reflects the real (about 10%) variation in the size of the gold nanoparticles found in the commercial sample.

Other nanoparticles composed of metallic materials such as silver (Ag), copper or cobalt or CdSe, may alternatively be used. Generally, any metal or semiconductor nanoparticle that has an affinity for thiols may be used. The nanoparticles may be up to 100 nm is size, and are preferably about 2-15 nm, for example 10 nm.

Figure 6A:
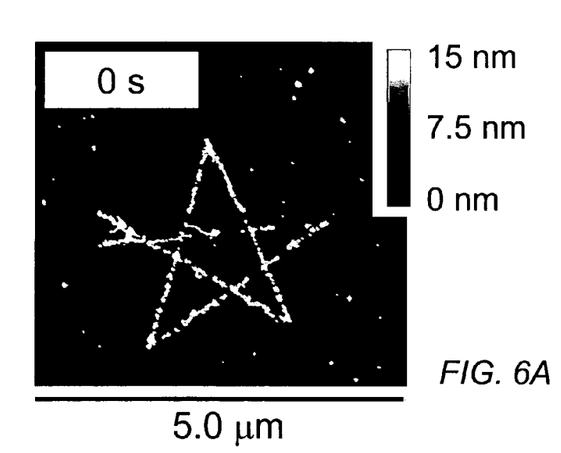
FIGS. 6A-C illustrate silver plating of a gold nanoparticle structure in accordance with one aspect of the present invention.
Figure 6B:
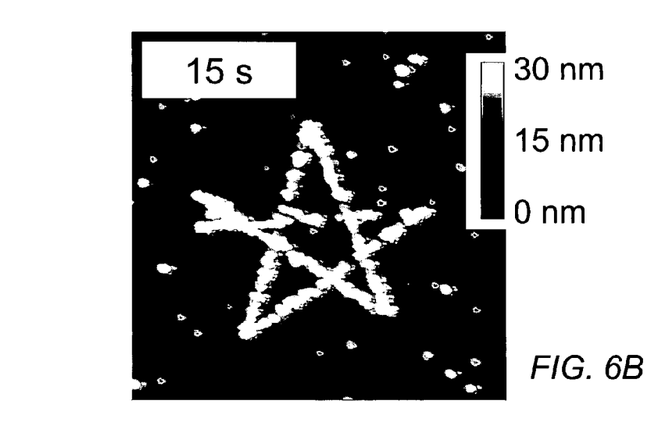
Figure 6C:
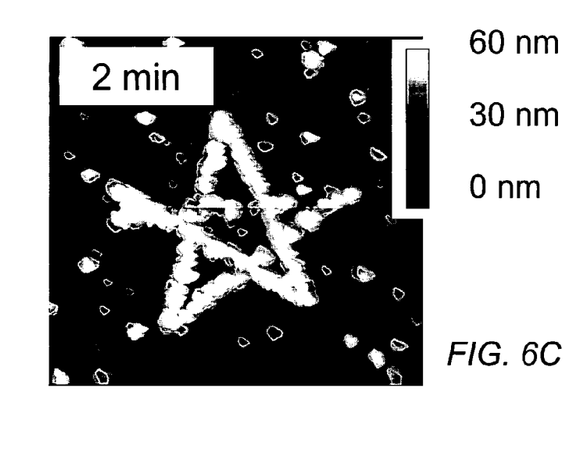

Standard plating techniques can also be used to transform the assembly of nanocrystals into nanowires or other continuous patterned features. Standard silver plating techniques, akin to those used in photography, may be used to thicken the lines or join the dots of nanoparticles. Plating causes the fusion of adjacent nanoparticles into a continuous metallic form. This is illustrated in FIGS. 6A-C wherein a silver plating is used to thicken the lines of a AuNP nanostructure having a star shape. The thickening of the lines is shown from the initial 10 nm AuNP nanostructure (0 s, FIG. 6A); to 15 s and 2 minutes of silver plating (FIGS. 6B and 6C, respectively). These images clearly demonstrate that plating occurs and that adjacent nanopraticles are fused to one another. Typical plating conditions use silver nitrate and hydroquinone in a pH3.5 citrate buffer. Using this process lines have been grown from 10 nm to 200 nm depending on the plating time.

Thus, the materials and methods of the invention can be used to fabricate lines a single particle in width as well as to control the placement of individual nanoparticles, and a method for the patternwise placement of nanoparticles with nanometer resolution is provided.

EXPERIMENTAL

The invention having been generally described, may be better understood by reference to the following examples, which are provided for purposes of illustration and are not to be considered limiting of the invention.

Example 1

Reactive Layer Precursor Synthesis

The protected thiol-containing reactive organic layer precursor 3,5-dimethoxy-α,α-dimethylbenzyloxycarbonyl-3-mercaptopropyltriethoxysilane was prepared as follows:

3,5-Dimethoxy-α,α-dimethylbenzylalcohol was prepared according to the literature procedure (Birr, C.; Lochinger, W.; Stahnke, G.; Lang, P *Liebigs Ann. Chem.* 1972, 763, 162-172. Cameron, J. F.; Fréchet, J. M. J. *J. Org. Chem.*, 1990, 55, 5919-22. A solution of 3,5-dimethoxy-α,α-dimethylbenzyl alcohol (3.93 g, 20.0 mmol) in pyridine (20 mL) and dichloromethane (20 mL) was cooled to 0° C. under an atmosphere of argon. To this solution was added p-nitrophenylchloroformate (4.84 g, 24.0 mmol) and the resulting heterogeneous mixture was allowed to stir at 0° C. for 18 h. Solvents were removed under vacuum and the crude material was passed through a plug of silica gel eluting with 85:10:5 hexanes:ethyl acetate:triethylamine. This intermediate (3,5-dimethoxy-α, α-dimethylbenzyl p-nitrophenyl carbonate) is not shelf stable and was used immediately in the next step without further purification. After evaporation of the chromatography solvents the residue was redissolved in acetonitrile (60 mL) and triethylamine (7.3 mL, 100 mmol). To this solution was added 3-mercaptopropyltriethoxysilane (5.64 mL, 22.0 mmol) and 4-dimethylaminopyridine (244 mg, 2.00 mmol) and the reaction mixture was allowed to stir under argon for 24 h. The solvents were removed under vacuum and the crude material was purified by chromatography on silica gel, eluting with 96:2:2 hexanes:ethyl acetate: triethylamine to provide the title compound as a colorless oil (2.39 g, 26%). $T_d$=160° C. Anal. Calcd. for $C_{21}H_{36}O_7SSi$ (460.66): C, 54.75; H, 7.88; S, 6.96. Found: C, 54.71; H, 7.96; S, 7.03. IR ν 2975, 2929, 2886, 1716, 1599, 1459, 1425, 1205, 1158, 1104, 1079, 960, 847, 790 cm$^{-1}$. $^1$H NMR (CDCl$_3$): δ 6.50 (2H, d), 6.35 (1H, t), 3.79 (6H, q), 3.78 (6H, s), 2.78 (2H, t), 1.75 (6H, s), 1.70 (2H, m), 1.21 (9H, t), 0.68 (2H, m) ppm. $^{13}$C NMR (CDCl$_3$): 169.02, 160.68, 147.83, 102.79, 98.67, 84.99, 38.33, 55.20, 33.80, 28.80, 23.55, 18.21, 9.79 ppm. HRMS (EI+): Calcd: 460.1951. Found: 460.1956.

Example 2

Selective Surface Activation of a Functional Monolayer for the Fabrication of Nanometer Scale Thiol Patterns and Directed Self-Assembly of Gold Nanoparticles Materials. All materials were obtained commercially and used as received unless otherwise noted. Pyridine, dichloromethane, and acetonitrile were distilled under nitrogen from calcium hydride immediately prior to use. Toluene was distilled from sodium/benzophenone ketyl immediately prior to use. An aqueous colloidal suspension of citrate ligated gold nanoparticles with an average diameter of 10 nm and a dispersity of ca. 10% was obtained commercially from Ted Pella, Inc. and used as received. All chromatography was performed using Merck Kieselgel 60 (230-400 mesh) silica.

Characterization: All $^1$H NMR and $^{13}$C NMR spectra were obtained with a Brucker AM-400 spectrometer in CDCl$_3$. Infrared spectra were obtained with Mattson Genesis II FTIR spectrometer with diffuse reflectance accessory (Pike). High-resolution electron impact mass spectrometry (HREI-MS) was performed at UC Berkeley MS Facilities. Elemental analysis was performed on a Perkin Elmer 2400 Series II combustion analyzer. Surface contact angles were measured by the sessile drop method on a Krüss Model G10 goiniometer at room temperature and ambient humidity using 18MΩ water. Ellipsometry was performed on a SENTECH Instruments GmbH SE400 ellipsometer.

Scanning force microscopy (SFM) images were obtained using a Nanoscope® IIIa (Digital Instruments, Santa Barbara, Calif.). Heavily doped silicon cantilevers (N, Phosphorous) with a resonant frequency of ca. 150 kHz were used in tapping mode for imaging and patterning.

Monolayer Formation and Patterning. Heavily doped (P, boron, 0.02-0.03 Ωcm) silicon wafers (Addison Engineering Inc. San Jose, Calif.) were marked using conventional lithography in order to relocate the AFM tip to the patterned regions. Lithographic patterning was performed according to the following procedure: OIR 897-10I (Arch Chemicals, Inc. Norwalk, Conn.) was spin coated onto an HMDS treated wafer at 4,100 rpm to produce a film 1.1 μm thick. This film was soft baked at 90° C. for 60 s. The resist was exposed at 365 nm with a dose of 135 mJ/cm$^2$ and developed with OPD 4262 (Arch Chemicals, Inc.) for 60 s. The resist was then hard baked at 120° C. for 10 min. Etching was performed on a STS Poly/Si Etcher using $SF_6$. For an over view of conventional lithography see: Thompson, L. F.; Willson, C. G.; Bowden, M. J. *Introduction to Microlithography* 2$^{nd}$ ed. Oxford University Press 1994.

Wafers were rinsed with acetone and then sonicated in acetone for 40 min to remove photoresist. The wafers where then submerged in boiling 30% hydrogen peroxide for 30 min to fully hydroxylate the surface. (Note: Hydrogen peroxide (30%) is a strong oxidizing agent and should be handled with appropriate precautions.) The wafers were thoroughly rinsed with distilled water, blown dry with nitrogen, and immediately placed in a 5 mg/mL solution of 3,5-dimethoxy-α,α-dimethylbenzyloxycarbonyl-3-mercaptopropyltriethoxysilane in dry toluene. After 24 h wafers were removed from the toluene solution, rinsed with acetone, and sonicated in acetone for 30 min. Finally, the wafers were rinsed with acetone followed by ethanol, blown dry with nitrogen and mounted on the AFM stage for patterning. Surfaces prepared in this fashion have a static water contact angle of 72° and an ellipsometric thickness of 0.7 nm. These surfaces have an RMS roughness (measured by AFM) of 0.154 nm.

Patterning with a scanning probe tool was performed in a manner analogous to that described in our pervious work (Fresco, Z. M.; Suez, I.; Backer, S. A.; Fréchet, J. M. J. *J. Am. Chem. Soc.* 2004, 126(7), 8374-8375). The amplitude set point was reduced to ca. 10% of the imaging set point and the grounded tip was translated across the surface while a positive 12 V potential was applied to the substrate. All patterning was performed in an inert atmosphere to avoid anodic oxidation of the underlying silicon substrate. Immediately after patterning, the substrate was immersed in an aqueous solution of DL-dithiothreitol (10 mg/mL) for 24 h, rinsed with distilled water and placed in an aqueous solution of citrate ligated AuNPs. After and additional 24 h the substrate was rinsed gently with distilled water and returned to the AFM for imaging.

Example 3

Patterning Free Thiol Lines and Fabricating 10 nm AuNP Lines on an Activated Organosulfur Monolayer Previous work in our laboratory has shown that a monolayer of DDZ (3,5-dimethoxy-α,α-dimethylbenzyloxycarbonyl) protected amines can be selectively deprotected by the application of a 12 V bias between the substrate and the tip of a scanning probe microscope. These free amine lines can be visualized by the subsequent self-assembly of carboxylic acid bearing macromolecules through ionic linkages. It has been postulated that the powerful local electric field produced by the tip causes heterolytic bond cleavage, leading to the release of a free amine. Although there is no precedent for such in the literature we have now discovered that a somewhat similar molecule containing a thiocarbonate type of linkage with a sulfur atom instead of a nitrogen is also able to produce an activated surface with free thiol groups. Given the larger size and lower electronegativity of sulfur when compared to nitrogen this finding is quite unexpected.

DDZ protected 3-mercaptopropyltriethoxysilane was prepared in two steps from 3,5-dimethoxy-α,α-dimethylbenzyl alcohol and 3-mercaptopropyltriethoxysilane using p-nitrophenyl chloroformate as shown in Scheme 1.

Figure 7:
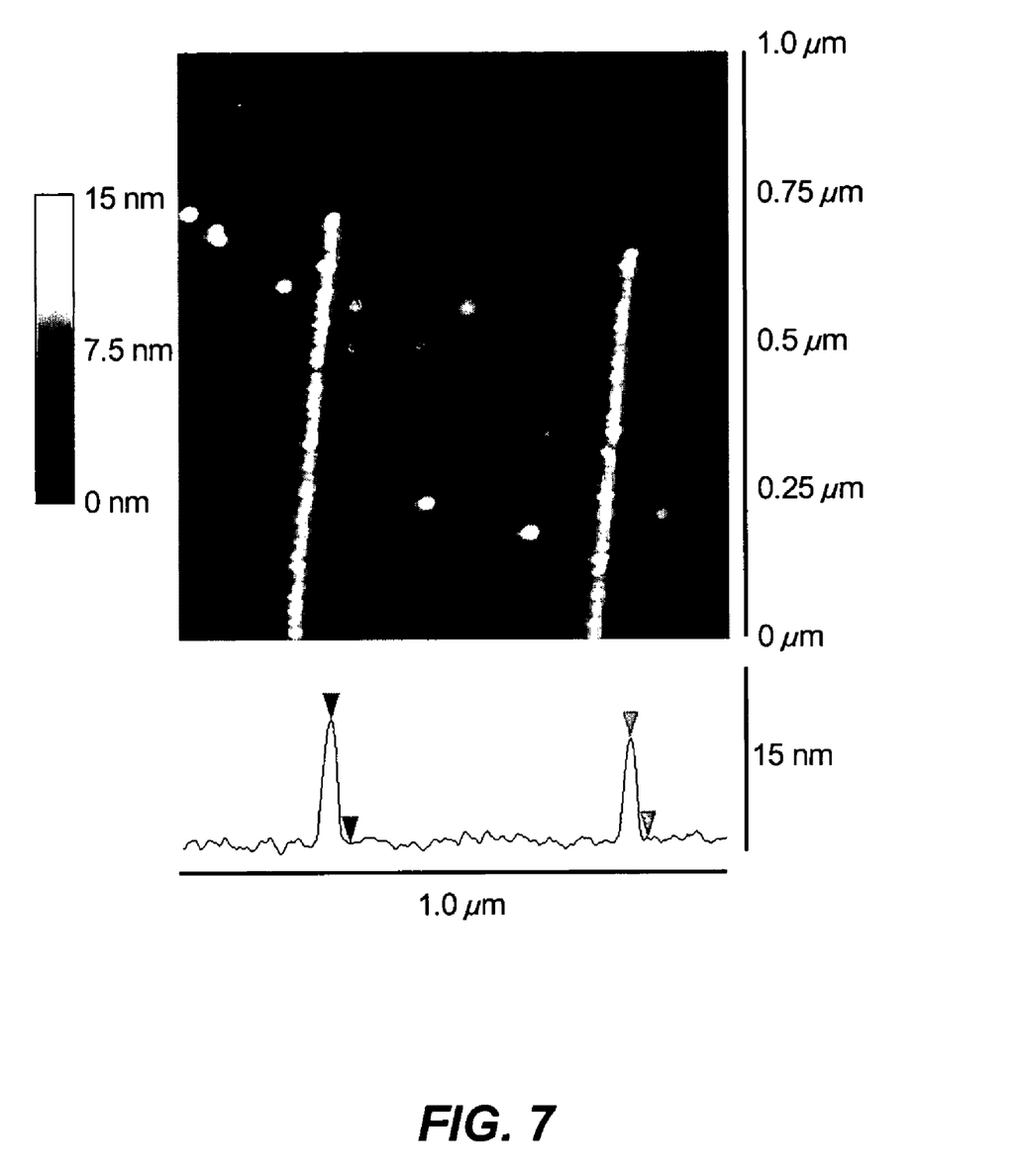
FIG. 7 shows an AFM image of lines of 10 nm gold nanoparticles in accordance with one aspect of the present invention, and their cross-sectional profile.

Monolayers were formed by immersing a freshly hydroxylated silicon surface in a solution of this monolayer precursor (0.5% in dry toluene). Patterning with a scanning probe tool was preformed in a manner similar to that used in our previous work. (Fresco, Z. M.; Suez, I.; Backer, S. A.; Fréchet, J. M. J. *J. Am. Chem. Soc.* 2004, 126, 8374-8375.). The amplitude set point was reduced to ca. 10% of the imaging set point and the grounded tip was traversed across the surface while a positive 12 V potential was applied to the substrate. All patterning was performed in an inert atmosphere to avoid anodic oxidation of the underlying silicon substrate. Immediately after patterning, the substrate was immersed in an aqueous solution of citrate ligated gold nanoparticles for 24 hours, rinsed gently and returned to the AFM for imaging. An AFM image of lines of 10 nm gold nanoparticles and their cross-sectional profile the are shown in FIG. 7.

Example 4

DTT Treatment to Enhance Affinity of AuNPs on an Activated Organosulfur Monolayer for Patternwise Placement with Nanometer Resolution Recent work in our laboratory has shown that under an inert atmosphere the application of a voltage bias between the tip of an AFM and a silicon substrate causes local activation of a self-assembled monolayer (SAM). We now outline the synthesis and characterization of a previously unreported organic monolayer containing a 3,5-dimethoxy-α,α-dimethylbenzyloxy-carbonyl (DDZ) protected thiol. The DDZ protecting group has previously been employed as a photocleavable group in organic synthesis and lithography. The accepted photochemical deprotection mechanism is homolytic bond cleavage followed by release of carbon dioxide and elimination of the tertiary carbocation to produce 3,5-dimethoxy-α-methylstyrene. The stability of the tertiary carbocation and the established ionic decomposition pathway were major factors in the choice of this protecting group. We hypothesized that the intense local electric field between the tip and the surface may induce decomposition via a pathway analogous to photochemical deprotection. The triethoxysilane moiety was employed to form self-assembled monolayers on hydroxylated silicon surfaces. The monolayers were formed by immersing a freshly cleaned and hydroxylated silicon wafer in a solution of 3,5-dimethoxy-α,α-dimethylbenzyloxycarbonyl-3-mercaptopropyltriethoxysilane in dry toluene. All patterning was subsequently performed in an atmosphere of dry nitrogen.

It was found that in some cases if the nanoparticle solution was applied to the surface immediately after patterning, precise gold features were not observed. It is likely that many of the newly exposed thiols are converted rapidly into disulfides either through exposure to atmospheric oxygen or during the patterning step itself. Based on this hypothesis, the surface was treated with an aqueous solution of a mild reducing agent, DL-dithiothreitol (DTT), in order to transform any disulfides back into thiols. Applying this surface treatment prior to exposure to the AuNP solution for self-assembly of the gold pattern vastly improved the adhesion of the AuNPs to the patterned regions and the sharpness of the pattern. While disulfides are known to bind to gold, the binding interaction is significantly weaker than that obtained with thiols. The importance of the DTT treatment is demonstrated by the fact that some surfaces showing no significant AuNP affinity immediately after AFM based patterning become active after being treated with DTT.

After mild reduction with aqueous DTT, the activated areas of the surface were effectively used to direct the self-assembly of AuNPs. This method allows fabrication of sharp lines of 10 nm AuNPs a single nanoparticle in width, as well as the placement of individual nanoparticles on the surface.

CONCLUSION

The present invention provides a simple and direct method for the facile patternwise deposition of AuNPs onto a surface with nanometer scale precision. This method relies on a functional organic layer containing a thiocarbonate that is cleaved under electrical stimulation to produce a thiol. Applying a positive 12 V potential to the substrate while translating a grounded AFM tip across the surface results in cleavage of the thiocarbonate to the free thiol. After mild reduction with aqueous DTT, the activated areas of the surface can effectively be used to direct the self-assembly of nanoparticles, including metallic or other conductive nanoparticles, such as AuNPs. This method allows fabrication of lines of 10 nm AuNPs a single nanoparticle in width, as well as the placement of individual nanoparticles on the surface. Patterns of closely spaced gold or other metallic or other conductive nanoparticles have potential applications in nanoelectronics and photonics for example as electrically conducting wires, as plasmon wave guides for photonic devices or as seeds for the growth of silicon nanorods, among others.

Although the foregoing invention has been described in some detail for purposes of clarity of understanding, it will be apparent that certain changes and modifications may be practiced within the scope of the invention. It should be noted that there are many alternative ways of implementing both the process and compositions of the present invention. Accordingly, the present embodiments are to be considered as illustrative and not restrictive, and the invention is not to be limited to the details given herein.

All references cited herein are incorporated by reference in their entirety for all purposes.

It is claimed:

1. An organosulfur compound, comprising:
   a group configured to bind to a surface;
   a protected thiol functional group bonded to the surface binding group; and
   a protecting group bonded to the protected thiol functional group via a polarized bond labile to field stimulated cleavage.

2. The compound of claim 1, wherein the group configured to bind to a surface is a silane.

3. The compound of claim 2, wherein the silane is selected from the group consisting of alkyl alkoxysilanes, alkyl chlorosilanes, amino silanes or sila-imidazoles.

4. The compound of claim 1, wherein the protecting group is 3,5-dimethoxy-α,α-dimethylbenzyloxycarbonyl.

5. The compound of claim 1, wherein the polarized bond labile to field stimulated cleavage is a thiocarbonate bond.

6. The compound of claim 1, wherein the compound is 3,5-dimethoxy-α,α-dimethylbenzyloxycarbonyl-3-mercaptopropyltriethoxysilane.

7. A protected thiol-containing reactive organic layer composition, comprising:
   a substrate surface; and
   a layer of an oganosulfur compound according to claim 1 bound to the substrate surface.

8. The composition of claim 7, wherein the substrate is a hydroxylated solid planar surface.

9. The composition of claim 8, wherein the substrate is a freshly hydroxylated silicon surface.

10. The composition of claim 9, wherein the organosulfur compound is 3,5-dimethoxy-α,α-dimethylbenzyloxycarbony-3-mercaptopropyltriethoxysilane.

11. The composition of claim 7, wherein the organosulfur layer is a top layer.

12. The composition of claim 7, wherein the organosulfur layer is a monolayer.

* * * * *